(12) United States Patent
Berner et al.

(10) Patent No.: US 8,342,194 B2
(45) Date of Patent: Jan. 1, 2013

(54) CONVEYOR WARE WASHER

(75) Inventors: Dietrich Berner, Waldstetten (DE);
Klaus Padtberg, Offenburg (DE)

(73) Assignee: Premark FEG L.L.C., Glenview, IL (US)

( * ) Notice: Subject to any disclaimer, the term of this patent is extended or adjusted under 35 U.S.C. 154(b) by 867 days.

(21) Appl. No.: 12/063,853

(22) PCT Filed: Aug. 10, 2006

(86) PCT No.: PCT/US2006/031112
§ 371 (c)(1),
(2), (4) Date: Jul. 24, 2008

(87) PCT Pub. No.: WO2007/024491
PCT Pub. Date: Mar. 1, 2007

(65) Prior Publication Data
US 2009/0211611 A1      Aug. 27, 2009

(30) Foreign Application Priority Data
Aug. 20, 2005 (DE) .......................... 10 2005 039 385

(51) Int. Cl.
*B08B 3/00* (2006.01)
(52) U.S. Cl. ........................ 134/48; 134/56 D; 134/58 D
(58) Field of Classification Search .................... None
See application file for complete search history.

(56) References Cited

U.S. PATENT DOCUMENTS

| | | | |
|---|---|---|---|
| 3,789,860 A | | 2/1974 | Katterheinrich et al. |
| 4,198,294 A | * | 4/1980 | Deane ........................... 210/650 |
| 4,765,906 A | * | 8/1988 | Downing et al. ............. 210/636 |
| 5,201,807 A | * | 4/1993 | Liljenberg et al. ........... 122/18.4 |
| 5,660,063 A | | 8/1997 | Lee et al. |
| 2002/0153021 A1 | | 10/2002 | Audet |
| 2005/0016910 A1 | | 1/2005 | Plante |

FOREIGN PATENT DOCUMENTS

| | | |
|---|---|---|
| DE | 3232057 | 3/1984 |
| DE | 4100164 | 4/1992 |
| DE | 4218958 | 12/1992 |
| DE | 29622760 | 7/1997 |
| DE | 29716444 | 1/1998 |
| DE | 19644438 | 4/1998 |
| DE | 10355139 | 6/2005 |
| DE | 10360906 | 7/2005 |
| EP | 150147 | 7/1985 |
| EP | 0560025 | 9/1993 |
| EP | 1042983 | 10/2000 |
| JP | 404089023 | 3/1992 |
| WO | 03/037801 | 5/2003 |
| WO | 2004/100755 | 11/2004 |
| WO | 2005/063109 | 7/2005 |

OTHER PUBLICATIONS

Woerter, Markus, Apr. 1998, DE 19644438, English machine translation.*

International Search Report issued regarding International Application No. PCT/US2006/031112 (Aug. 8, 2007).

(Continued)

*Primary Examiner* — Michael Barr
*Assistant Examiner* — Jason Ko
(74) *Attorney, Agent, or Firm* — Thompson Hine LLP (57) ABSTRACT

Conveyor ware washer comprising a water treatment device (70) for treating sprayed wash liquid in such manner that the treated liquid is of potable quality of water from the microbiological point of view and hence can be used as final rinse liquid or as part of a final rinse liquid.

12 Claims, 5 Drawing Sheets

OTHER PUBLICATIONS

Written Opinion issued regarding International Application No. PCT/US2006/031112 (Aug. 8, 2007).
International Search Report issued regarding International Application No. PCT/US2006/030408 (Dec. 19, 2006).
Written Opinion issued regarding International Application No. PCT/US2006/030408 (Dec. 19, 2006).
International Search Report issued regarding International Application No. PCT/US2006/031114 (Aug. 8, 2007).
Written Opinion issued regarding International Application No. PCT/US2006/031114 (Aug. 8, 2007).
International Preliminary Report on Patentability issued regarding International Application No. PCT/US2006/030408 (Feb. 20, 2008).
International Preliminary Report on Patentability issued regarding International Application No. PCT/US2006/030114 (Feb. 20, 2008).
Machine Translation of DE 19644438.
Machine Translation of DE 10360906.
ISR—PCT/US2006/030408 mailed Dec. 19, 2006.
International Preliminary Report on Patentability issued regarding International Application No. PCT/US2006/031112 (Feb. 28, 2008).

* cited by examiner

CONVEYOR WARE WASHER

The invention concerns a conveyor ware washer, particularly a commercial conveyor ware washer of the type commonly configured in the form of a flight-type ware washer or in the form of a rack conveyor ware washer.

Conveyor ware washer in the form of a flight-type ware washer or a rack conveyor ware washer comprising, for example, at least one wash zone, which is provided with wash nozzles for wash liquid, and which is provided with a wash liquid re-circulation line, where the latter includes a wash tank for collecting at least a part of the sprayed wash liquid and a wash liquid supply pipe equipped with a pump for feeding wash liquid from the wash tank to the wash nozzles; a final rinse zone with final rinse nozzles, to which final rinse liquid can be fed from a final rinse liquid feeding device; a conveyor system for transporting wash ware through the zones, where the direction of the transportation of the conveyor system is aimed from the at least one wash zone to the final rinse zone; where the zones are interconnected with each other in form of a liquid cascading system, in which the sprayed liquid flows against the direction of transportation from the final rinse zone to the at least one wash zone up to the wash zone which is the first wash zone in the direction of transportation.

For example, conveyor ware washers are known to be exemplified in the following documents: U.S. Pat. No. 3,789,860; U.S. Pat. No. 4,231,806; DE 196 44 38 C2; DE 198 29 560 C2.

In the case of above-mentioned conveyor ware washers, fresh water is directed, following the principle of cascading, starting from fresh water final rinsing through several wash tanks into a drain. In this process, the water removes soil that is carried by the wash ware to be cleaned into the dish washer. This water is drained off as waste water at the end of the cascading system directly or indirectly into the sewage system, mostly through an oil separator.

It would be desirable to provide a conveyor ware washer in such manner that consumption of potable water is reduced. In one arrangement, this purpose is fulfilled by the features as defined in claim 1.

By treating wash water in such manner that it can be either considered as potable water from a microbiological point of view or, it can be mixed with normal potable water in a ratio that the resulting water is of potable quality of water from a microbiological point of view, in order that the so treated water can be used as fresh water in the fresh water final rinsing operation, water and energy consumption can be reduced.

The treatment of water may be performed at least by means of a micro-filtration system and/or at least by means of an ultra-filtration system. If necessary, the pH value can be set to a neutral range or close to the neutral range. If additionally required, the level of hygiene can be ensured by adding ozone as a disinfecting component.

An embodiment of the invention is described in the following at hand of preferred embodiments as examples with reference to the enclosed drawings. The drawings show in.

By way of example, the conveyor ware washer can be a flight-type ware washer, in which the wash ware to be cleaned is carried on a conveyor belt through the machine, or a rack conveyor ware washer, in which the wash ware is carried on racks on the transportation device through the machine.

Figure 1:
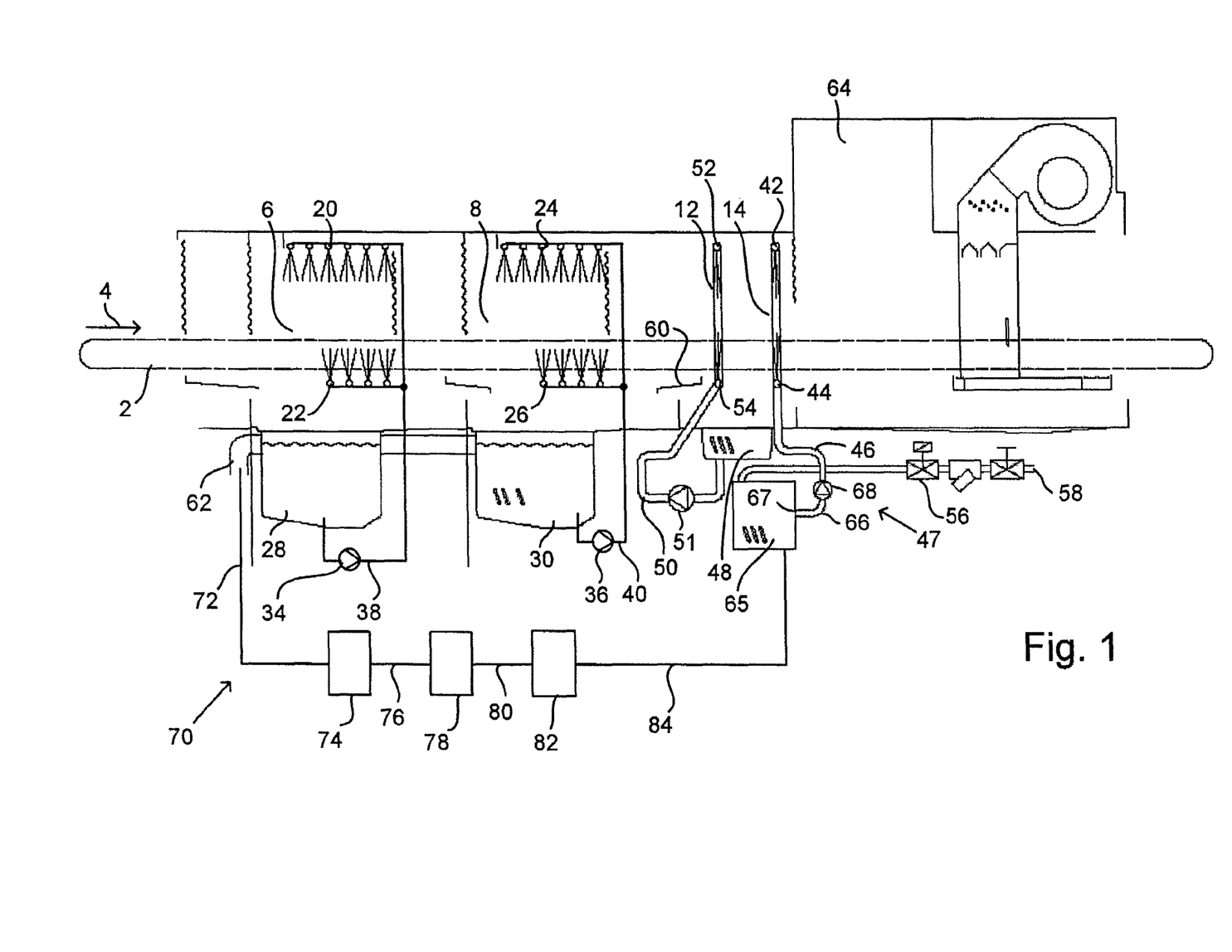
FIG. 1 a schematic lateral view of a section of a conveyor ware washer.

The conveyor ware washer as shown in FIG. 1 includes a transportation device 2 where the direction of transportation 4 (the "transport direction") is indicated by an arrow. The wash ware not shown here can be of any type, for example, plates, cups, glasses, cutlery, trays, pots or pans.

The conveyor ware washer includes at least one or, for example, according to the drawings two (or more) wash zones 6 and 8 arranged sequentially in the direction of transportation 4 for washing the wash ware with wash liquid, followed by a post-wash zone 12 for further washing the wash ware with post-wash liquid and, thereafter, at least one final rinse zone 14 for the final rinse for the wash ware with the final rinse liquid.

The wash liquid is water to which a detergent is added. Final rinse liquid can be fresh water with or without a rinse aid.

In each wash zone 6 and 8, upper and lower wash nozzles 20, 22 and 24, 26 are located for spraying wash liquid over the wash ware that is located on the transportation device 2. The wash zones 6 and 8 are each provided with a wash tank 28 and 30, in which wash liquid sprayed by the wash nozzles 20, 22 and 24, 26 is collected. The wash liquid is re-circulated from the wash tanks 28 and 30 back to the wash nozzles 20, 22 and 24, 26 through a wash liquid supply pipe 38 and 40 by means of a pump 34 and 36. The wash liquid supply pipe 38 and 40 and the associated wash tanks 28 and 30 compose wash liquid re-circulation lines 28/38 and 30/40. Each wash liquid re-circulation line 28/38 and 30/40 along with the related wash zone 6 and 8 and their wash nozzles 20, 22 and 24, 26 form a wash liquid re-circulation system.

The final rinse zone 14 is provided with upper and lower final rinse nozzles 42 and 44, into which final rinse liquid can be fed through a final rinse liquid supply pipe 46 belonging to a final rinse liquid supply device 47. The final rinse liquid sprayed by the final rinse nozzles 42 and 44 is collected in a post-wash tank 48 in the post-wash zone 12. The post-wash liquid is fed from the post-wash tank 48 by means of a pump 51 through a post-wash liquid supply pipe 50 to the upper and lower post-wash nozzles 52 and 54 within the post-wash zone 12. The post-wash liquid sprayed by the post-wash nozzles 52 and 54 partly reaches the post-wash tank 48 and partly the last wash tank 30 through a guide element 60. Therefore, the post-wash liquid is the pre-used final rinse liquid.

For this reason, the post-wash zone 12 can also be considered as a pre-rinse zone, the post-wash liquid as pre-rinse liquid, the post-wash tank 48 as a pre-rinse tank and the post-wash nozzles 52 and 54 as pre-rinse nozzles.

The wash tanks 28 and 30 and the post-wash tank 48 form a liquid cascading system, in which the liquid overflows from one to the other tank in the opposite direction of transportation 4 of the transportation device 2. Therefore, the liquid runs from the post-wash tank 48 into the last wash tank 30 in the direction of transportation and from this into the previous wash tank 28. The last wash tank 28 in the direction of flow, which is the first wash tank in the direction of transportation 4, is preferably provided with a drain 62 for the soiled liquid.

A drying zone 64 can be arranged in the direction of transportation 4 after the final rinse zone 14 for drying the cleaned wash ware.

The invention concerns also conveyor ware washers that do not possess a post-wash zone 12. In such case, the liquid sprayed by the final rinse nozzles 42 and 44 in the final rinse zone 14 is intercepted by, for example, a guide element, a base or a floor drain pan or a tank in the final rinse zone 14 and transferred to the last wash tank 30 in the direction of transportation 4.

The final rinse liquid supply device 47 can possess a fresh water connection 56 to link to a fresh water supply pipe 58. In addition to this, a water heater 65, preferably a boiler, can be provided for heating the final rinse liquid.

If the water pressure in the fresh water supply pipe 58 is sufficiently high and constant, the final rinse liquid supply pipe 46 belonging to the final rinse nozzles 42 and 44 can be connected to an outlet 67 of the water heater 65 without an intermediate pump. However, if the fresh water pressure is insufficient for supplying final rinse liquid to the final rinse liquid spray nozzles 42 and 44, then a pump 68 can be placed between the fresh water supply pipe 58 and the final rinse liquid supply pipe 46. The pump 68 can be placed between the outlet 67 of the water heater 65 and the final rinse liquid supply pipe 46 either directly or over a connecting pipe 66.

Rinse aids can be added to the fresh water in the fresh water supply pipe 58 at every suitable point on the upstream from the final rinse nozzles 42, 44.

As per the invention, a water treatment device 70 is provided for receiving and treating the sprayed wash liquid from a particular one of the at least one wash zones 6, 8 in such manner that the treated liquid is of potable quality of water from the microbiological point of view and for delivering the treated liquid to the final rinse liquid supply device 47 where the final rinse liquid supply device 47 is designed in such manner that it can feed final rinse liquid to the final rinse nozzles 42 and 44 which is at least partly formed by the treated liquid.

As per the preferred embodiment of the invention, the particular wash zone, from which the water treatment device 70 receives the sprayed wash liquid, is the first wash zone 6 in the direction of the wash ware transportation 4 of the transportation device 2. This first wash zone 6 is the last wash zone in the direction of flow of wash liquid in the liquid cascading system, as this direction of flow is opposite to the direction of transportation 4. The treatment of wash liquid that is sprayed in the first wash zone in the direction of transportation 4, results in a complete recycling of the water used in the ware washer. However, the invention can also be used for partial recycling of water by arranging the water treatment device 70 for receiving and treating the liquid sprayed in another wash zone, for example, in the second wash zone 8 in the direction of the transportation 4.

The treated liquid can be released to the final rinse liquid supply device 47 at different locations, for example, as shown in FIG. 1 to 4 of the drawings into the boiler 65 or at another location on the upstream of the final rinse pump 68 or into the final rinse liquid supply pipe 46 which is connected to the final rinse nozzles 42 and 44 of the final rinse zone 14.

As per a preferred embodiment, the water treatment device 70 includes in the direction of flow of liquid, for example, a receptor pipe 72, a filtration device 74 in the form of a micro-filtration device and/or in the form of an ultra-filtration device, a connecting pipe 76 for the filtered liquid, an ozone supplementing device 78 for adding ozone ($O_3$) to the filtered liquid, a connecting pipe 80 for the ozone-enriched liquid, a pH value neutralizing device 82 for at least partially neutralizing the pH value of the ozone-enriched liquid, and a release pipe 84 for releasing the so treated liquid to the final rinse liquid supply device 47.

Figure 2:
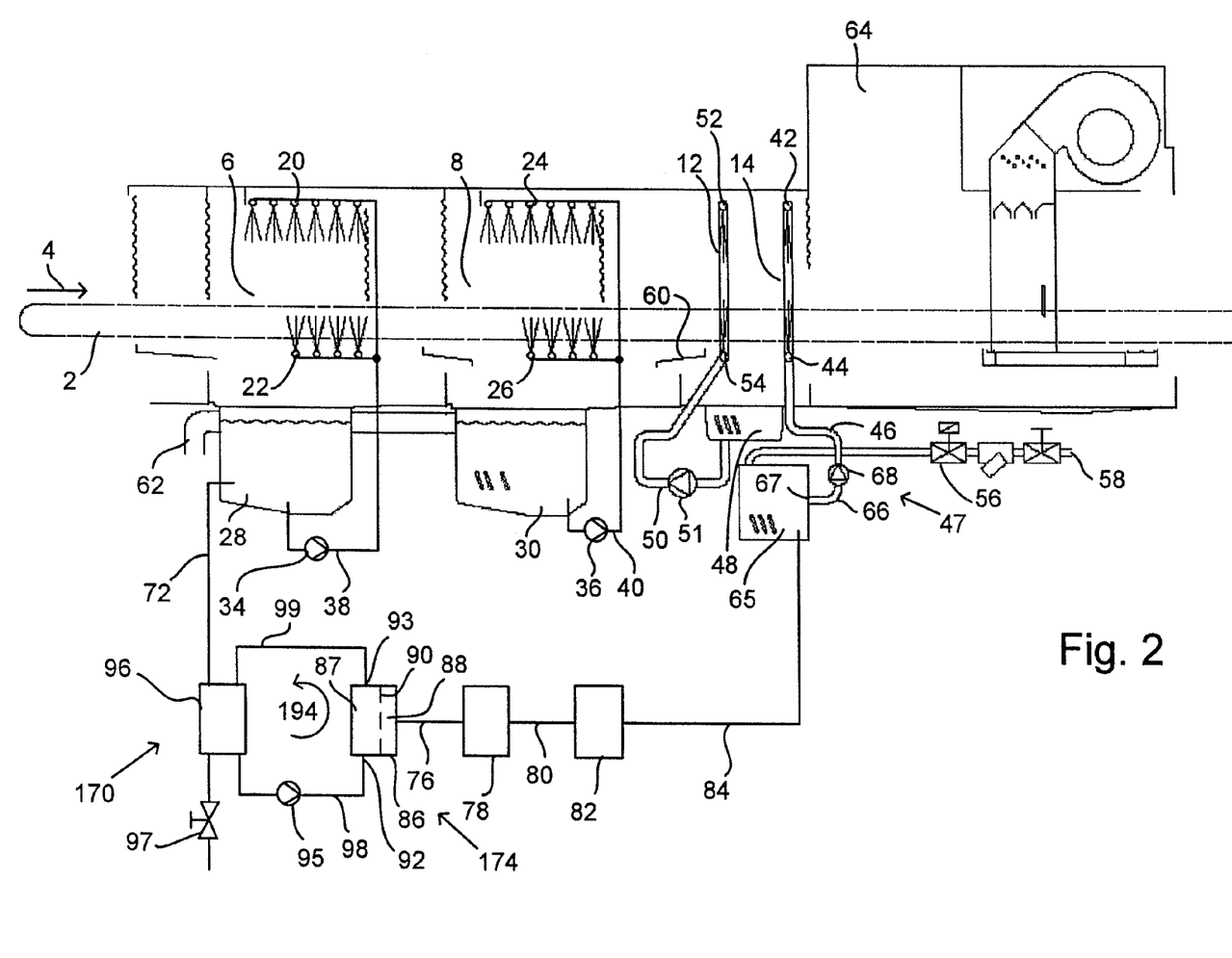
FIG. 2 a similar view of another embodiment of a conveyor ware washer.
Figure 3:
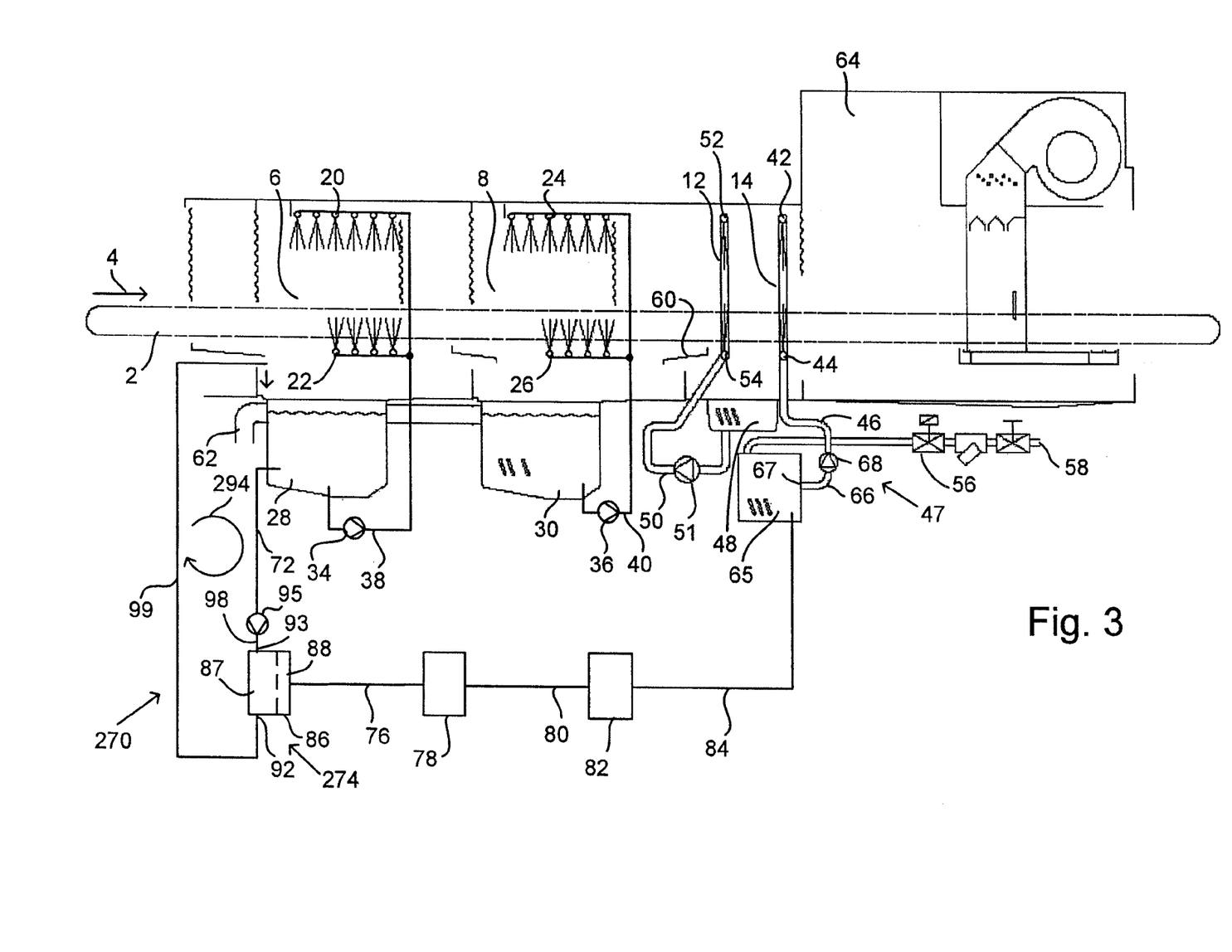
FIG. 3 a similar view of yet another embodiment of a conveyor ware washer.
Figure 4:
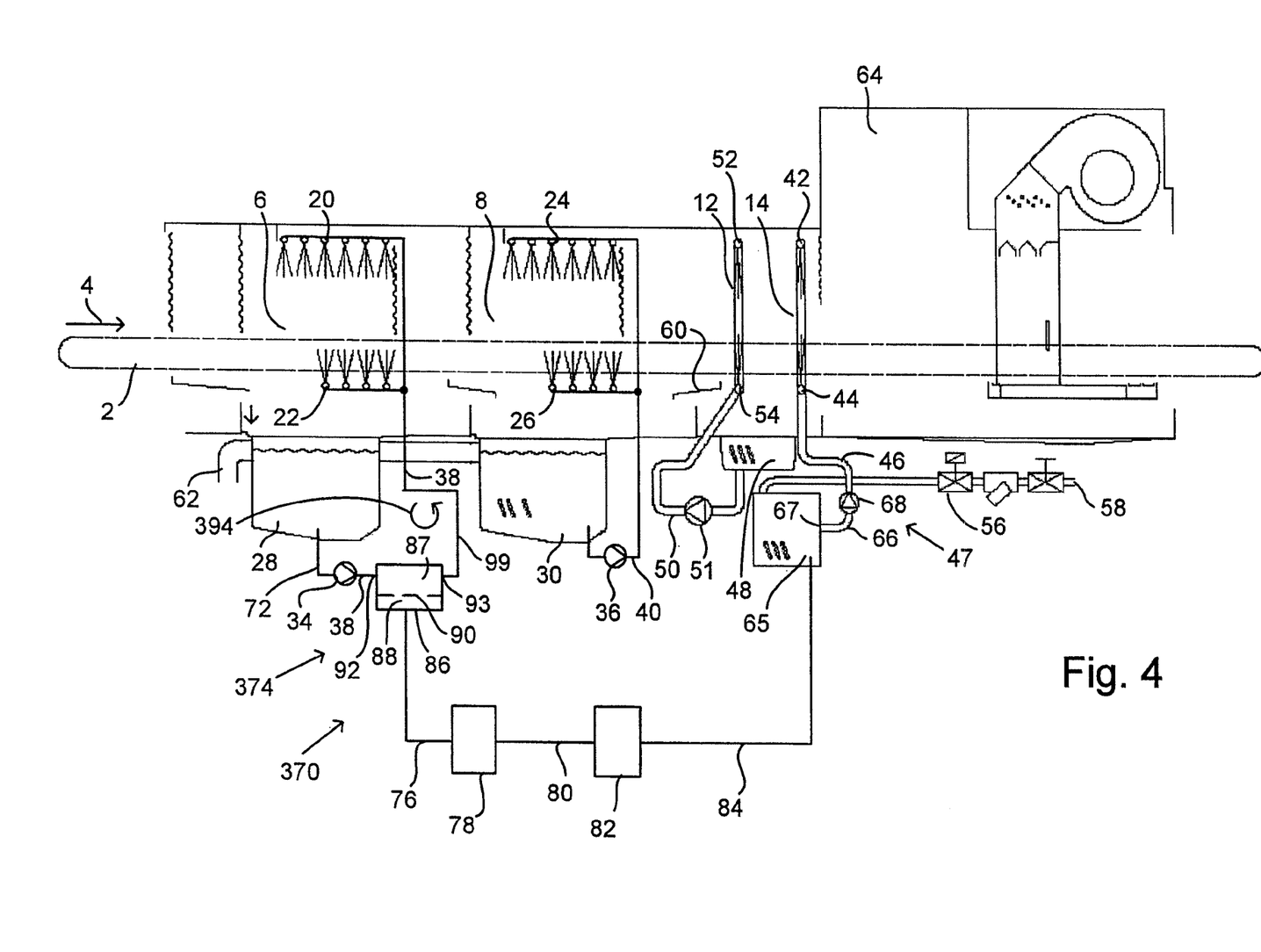
FIG. 4 schematically a similar view of yet another embodiment of a conveyor ware washer, FIG. 5 schematically a embodiment of an ozone supplementing device for the conveyor ware washer, FIG. 6 a schematic illustration of another embodiment of an ozone supplementing device for the conveyor ware washer, FIG. 7 yet another embodiment of an ozone supplementing device for the conveyor ware washer.

As per FIG. 1, the receptor pipe 72 for receiving the sprayed wash liquid can be connected to the drain 62 of the last wash zone 6 in the direction of flow of liquid of the cascading or to the wash tank 28 of this last wash zone 6, as shown in FIGS. 2, 3 and 4, or as per yet another design, to the wash tank of another wash zone, for example to the wash tank 30 of the penultimate wash zone 8 in the direction of flow in the cascading system or of another wash zone.

Normally, the sprayed wash liquid has a pH value of approximately 10 to 11. It is reduced by the pH value neutralizing device 82 preferably to a pH value in the range of 7 to 8. These values do not rule out the use of other values, for example, a reduction of pH value by means of the pH value neutralizing device 82 to a value less than 7 or higher than 8.

For example, an acidic Ion exchanger resin can be used as neutralizing substance for neutralizing the pH value, by which the liquid to be neutralized is pressed through. It is evident to a technical expert that other ion exchanging substances can also be used. Another method for neutralizing the pH value is to add a buffer solution to the wash liquid to be neutralized.

However, a pH value neutralizing device 82 is not required if the wash liquid to be treated has a pH value close to 7. Again, this depends on what type of wash ware is being cleaned, what type of soil particles it contains, and it can also depend on the type of rinse aid that is added to the final rinse liquid, if necessary, and on the detergent that is added to the wash liquid.

The filtration device 74 can be designed in different ways. A few examples are shown in FIGS. 2, 3 and 4.

As per the preferred design of the invention, the filtration device 74 includes a cross-flow filter with at least one microfiltration element and/or at least one ultra-filtration element for filtering the wash liquid.

Elements shown in FIGS. 2, 3 and 4 which correspond to the elements in FIG. 1 as regards the function, however, are designed differently, are provided with the same, albeit an incremented reference number of 100, 200 or 300.

In the case of the water treatment device 170 shown in FIG. 2 as per the invention the filtration device 174 includes a cross-flow filter 86. The cross-flow filter 86 includes at least a primary chamber 87 and at least a secondary chamber 88 which are separated from each other by at least one microfiltration element or at least one ultra-filtration element 90. The primary chamber 87 is flushed through from an inlet 92 to an outlet 93 by the wash liquid to be cleaned, which is fed to the inlet 92 by means of a pump 95 from the wash tank 28 over an intermediate container 96, which in turn receives sprayed wash liquid over the receptor pipe 72 from the wash tank in the first wash zone 6 in the direction of transportation 4. The outlet 93 of the primary chamber 87 is also connected to the intermediate container 96. Thus, the primary chamber 86, the intermediate container 96 and the pump 95 form a primary chamber re-circulation system 194. The primary chamber 92 is connected over a primary chamber inlet pipe 98, with which the pump 95 is integrated, to the intermediate container 96, where the pump 95 feeds in the direction from the intermediate container 96 to the primary chamber inlet 92. The primary chamber outlet 93 is connected to the intermediate container 96 over a primary chamber outlet pipe 99.

The intermediate container 96 can be designed as a soil collector, from which accumulating soil can be continuously or intermittently removed. For example, the intermediate container 96 can be provided with an outlet valve 97 or include a detachable filter element for removal of soil.

As per another embodiment of the invention not shown here, the outlet 93 of the primary chamber 87 is not integrated with a primary chamber re-circulation system 194, but connected to a drain for disposal of that part of the wash liquid which does not reach the secondary chamber 88 through the at least one micro-filtration element and/or one ultra-filtration element 90 and flow from there into the connecting pipe 76 for the filtered liquid.

FIG. 3 shows a water treatment device 270 with a micro-filtration device 274 or an ultra-filtration device 274, which does not include an intermediate container 96. Here the primary chamber 87 of the cross-flow filter 86, the pump 95 and the wash tank 98 in the last wash zone 6 in the direction of flow of the cascading system form a primary chamber re-circulation system 294. The same parts as in FIG. 2 are provided with the same reference numbers in FIG. 3. The primary chamber inlet pipe 98 is connected to the pressure side of the pump 95. The suction side of this pump 95 is connected to the wash tank 98 of the wash zone 6 by means of the wash water intake pipe 72. The primary chamber outlet pipe 99 opens into the same wash tank 28.

The micro-filtration device 374 or the ultra-filtration device 374 of a water treatment device 370 in FIG. 4 is connected to the wash liquid re-circulation line 28/38 of the first wash zone 6 in the direction of transportation 4. As per FIG. 4, a cross-flow filter 86 is again provided. Its primary chamber 87 can be aligned in the upstream or downstream direction of the pump 34 of this wash liquid re-circulation line 28/38, for example, as per FIG. 4 on the upstream of this pump 34 at the beginning or in a section of the wash liquid supply pipe 38 of this wash liquid re-circulation line 28/38. The primary chamber 87 of the cross-flow filter 86 is integrated with the path of flow of the wash liquid of the wash liquid supply pipe 38 and flushed through by this wash liquid in the direction from its inlet 92 to its outlet 93. The intake pipe 72 is formed by an upstream section of the wash liquid supply pipe 38 and connected to the primary chamber inlet 92. The remaining section of the wash liquid supply pipe 38 is connected to the primary chamber outlet 93 and, therefore, at the same time it constitutes also the primary chamber outlet pipe 99.

A filtration device 74 and 174 or 274 and 374 is always required in the form of at least one micro-filtration device and/or one ultra-filtration device for treating the sprayed wash liquid, if it contains particles that must be filtered off.

The ozone supplementing device 78 is always necessary if adding ozone to the sprayed wash liquid is necessary for achieving a potable quality of water from the microbiological point of view, before it is led to the final rinse supply device 47. The ozone supplementing device 78 is placed preferably in the path of flow of the wash liquid to be treated between the filtration device 74 or 174 or 274 or 374 and the pH value neutralizing device 82. It can be used in different designs. Some examples of this are shown in FIGS. 5, 6 and 7.

Figure 5:
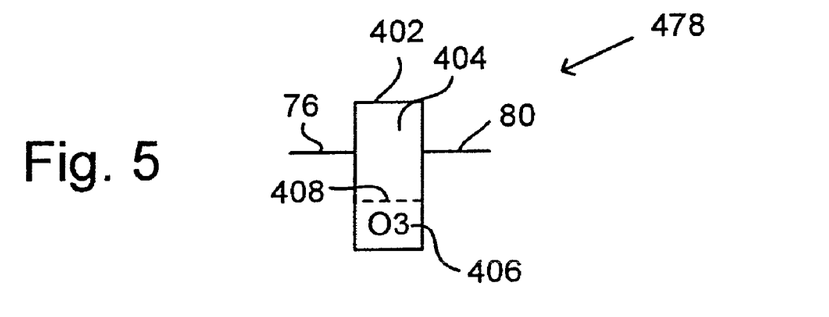

The ozone supplementing device 478 in FIG. 5 includes in the path of flow of the wash liquid to be treated a storage container 402, which has a wash liquid chamber 404 flushed through by wash liquid to be cleaned and an ozone chamber 406, which are separated from each other by a gas-permeable membrane 408. Ozone, for example, in the form of an ozone and air mixture, flows from the ozone chamber 406 through the gas-permeable membrane 408 into the wash liquid to be treated in the wash liquid chamber 404 of the storage container 402.

Figure 6:
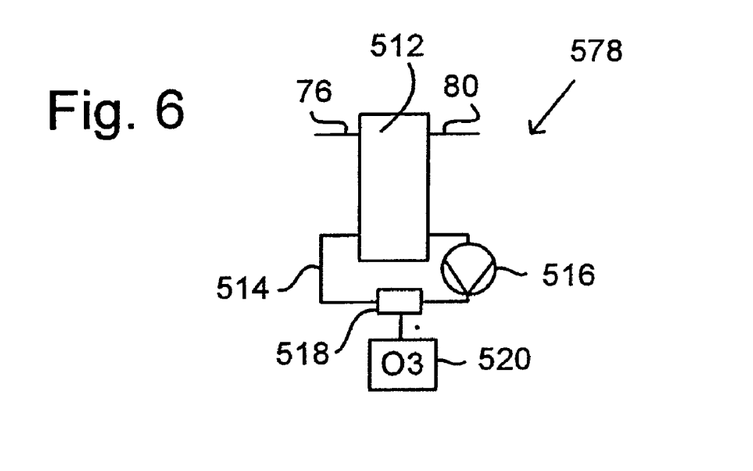

The ozone supplementing device 578 in FIG. 6 includes a container 512 which is flushed through by the wash liquid to be cleaned and is also part of a wash liquid re-circulation system 514 flowing through it. The wash liquid re-circulation system 514 has a pump 516 and a venturi element or an injector element 518. The venturi element or injector element 518 suctions ozone from a source of ozone 520, for example an ozone and air mixture, into the re-circulated part of the wash liquid, which herewith receives ozone and thereafter transfers ozone in the storage container 512 to that part of the wash liquid which is in the storage container 512.

Figure 7:
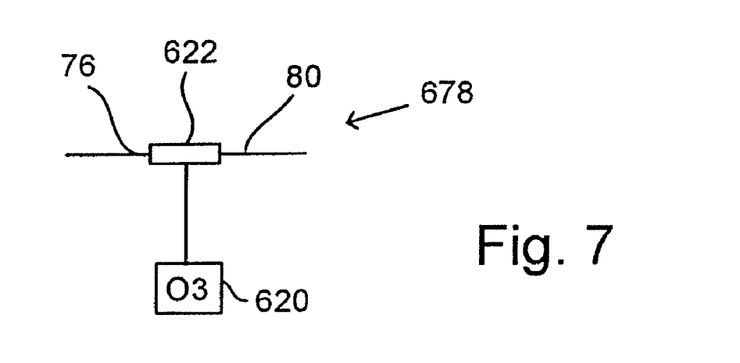

The ozone supplementing device 678 in FIG. 7 includes a venturi nozzle or an injector 622 in the path of flow of the wash liquid between the connecting pipe 76 for filtered wash liquid and the connecting pipe 80 for ozone-enriched liquid. This venturi element or the injector element 622 generates vacuum by means of the filtered wash liquid flowing through it and suctions thereby ozone, for example an ozone and air mixture, from a source of ozone 620 into the liquid flowing through it.

The invention claimed is:

1. A conveyor ware washer, comprising:
  at least one wash zone having wash nozzles for spraying wash liquid and a wash liquid re-circulation path that includes a wash tank for collecting at least a part of sprayed wash liquid and a wash liquid supply pipe with a pump for feeding wash liquid from the wash tank to the wash nozzles;
  a final rinse zone with final rinse nozzles for spraying final rinse liquid fed from a final rinse liquid supply device, the final rinse zone downstream of the wash zone;
  a transportation device for carrying wares through the wash zone and final rinse zone in a transport direction from the wash zone to the final rinse zone;
  wherein the wash zone and final rinse zone are interconnected with each other to form a liquid cascading system, in which sprayed liquid flows from the final rinse zone to the wash zone;
  characterized by a water treatment device connected for receiving and treating sprayed wash liquid from the wash zone, the water treatment device configured in such manner that the treated liquid is of potable quality of water from the microbiological point of view, and the water treatment device connected for releasing the treated liquid to the final rinse liquid supply device, where the final rinse liquid supply device is connected to feed final rinse liquid, which is formed at least partly by the treated liquid, to the final rinse nozzles of the final rinse zone,
  wherein the final rinse liquid supply device includes a boiler from which final rinse liquid is fed to the final rinse nozzles, the boiler including a fresh water supply input line, the boiler further including a treated water input line running from the water treatment device and, connected to release the treated liquid into the boiler for mixing with fresh water and for heating prior to the treated liquid being delivered to the final rinse nozzles.

2. The conveyor ware washer of claim 1 characterized in that:
  a post-wash zone is arranged between the wash zone and the final rinse zone, the transportation device travels through the post-wash zone, the post-wash zone is included in the liquid cascading system, a post-wash tank is assigned to the post-wash zone, both final rinse liquid sprayed in the final rinse zone and at least a part of post-wash liquid sprayed by post-wash nozzles in the post-wash zone are collected in the post-wash tank, post-wash liquid from the post-wash tank can be transferred to the post-wash nozzles, and post-wash liquid from the post-wash tank can flow along the liquid cascading system into the wash tank of the wash zone.

3. The conveyor ware washer of claim 1 characterized in that the water treatment device comprises a micro-filtration device or an ultra-filtration device for the filtration of sprayed wash liquid.

4. The conveyor ware washer of claim 3 characterized in that the micro-filtration device or the ultra-filtration device comprises a cross-flow filter for the micro-filtration or ultra-filtration of sprayed wash liquid.

5. The conveyor ware washer of claim 4 characterized in that the cross-flow filter has at least one primary chamber and at least one secondary chamber, which are separated from each other by at least one micro-filtration element or at least one ultra-filtration element, where the primary chamber is integrated with a primary chamber liquid circulation, into which sprayed wash liquid can be fed from the wash zone, and where the at least one secondary zone receives the filtered part of the wash liquid passing through the micro-filtration element or through the ultra-filtration element into it.

6. The conveyor ware washer of claim 3 characterized in that the treatment device has an ozone supplementing device to introduce ozone or an ozone and air mixture into the filtered part of the wash liquid.

7. The conveyor ware washer of claim 6 characterized by a pH value neutralizing device for neutralizing at least partly the pH value of the filtered wash liquid.

8. The conveyor ware washer of claim 7 characterized in that the pH value neutralizing device is placed downstream of the ozone supplementing device in the path of flow of the ozone-enriched liquid and designed for at least partially neutralizing the pH value of the ozone-enriched liquid.

9. The conveyor ware washer of claim 1 characterized in that the wash zone is a first wash zone in the transport direction, and at least one additional wash zone is located between the first wash zone and the final rinse zone.

10. The conveyor ware washer of claim 1 wherein the wash tank holds a supply of soiled wash liquid that is recirculated for spraying by the wash nozzles.

11. A conveyor ware washer, comprising:
a transportation device for carrying wares in a transport direction through multiple spray zones including:
a wash zone having wash nozzles for spraying wash liquid and a wash liquid re-circulation path that includes a wash tank for collecting at least a part of sprayed wash liquid and a wash liquid supply pipe with a pump for feeding wash liquid from the wash tank to the wash nozzles;
a final rinse zone having final rinse nozzles for spraying final rinse liquid and a final rinse liquid path that includes a boiler and a final rinse liquid pipe with a pump for feeding final rinse liquid from the boiler to the final rinse nozzles, the final rinse zone downstream of the wash zone, the boiler including a fresh water supply input line and a treated water input line;
a post-wash zone immediately upstream of the final rinse zone and having an associated post-wash tank, both final rinse liquid sprayed in the final rinse zone and at least a part of post-wash liquid sprayed by post-wash nozzles in the post-wash zone are collected in the post-wash tank, a pump and post-wash liquid supply pipe connected to deliver post-wash liquid from the post-wash tank to the post-wash nozzles;
wherein the wash tank and post-wash tank are interconnected with each other to form a liquid cascading system, in which sprayed liquid flows from the final rinse zone into the post-wash tank and subsequently to the wash tank;
a water treatment device connected for receiving and treating sprayed wash liquid from the wash zone in such manner that the treated liquid is of potable quality of water from the microbiological point of view, the water treatment device including a water filtration device, the water treatment device connected via the treated water input line to release the treated liquid into the boiler for mixing with fresh water and heating prior to the treated liquid being delivered from the boiler to the final rinse nozzles, the final rinse nozzles being the last liquid spraying nozzles of the conveyor ware washer relative to the transport direction;
wherein the wash tank holds a supply of soiled wash liquid that is recirculated for spraying by the wash nozzles.

12. The conveyor ware washer of claim 11, wherein:
the wash zone is a first wash zone, the wash tank is a first wash tank and the wash nozzles are first wash nozzles;
a second wash zone is located between the first wash zone and the post-wash zone, a second wash tank associated with the second wash zone for collecting at least a part of sprayed wash liquid sprayed by second wash nozzles in the second wash zone;
the liquid cascading system includes the second wash tank such that sprayed liquid flows from the final rinse zone into the post-wash tank and subsequently to the second wash tank and subsequently to the first wash tank.

* * * * *